(12) United States Patent
Rademacher et al.

(10) Patent No.: US 9,114,082 B2
(45) Date of Patent: Aug. 25, 2015

(54) NANOPARTICLE PEPTIDE COMPOSITIONS

(71) Applicant: Midatech Limited, Abingdon (GB)

(72) Inventors: Thomas Rademacher, Oxfordshire (GB); Phillip Williams, Oxfordshire (GB)

(73) Assignee: Midatech Limited, Abingdon, Oxford (GB)

( * ) Notice: Subject to any disclaimer, the term of this patent is extended or adjusted under 35 U.S.C. 154(b) by 0 days.

(21) Appl. No.: 14/174,251

(22) Filed: Feb. 6, 2014

(65) Prior Publication Data

US 2014/0249081 A1 Sep. 4, 2014

(30) Foreign Application Priority Data

Mar. 4, 2013 (GB) .................................. 1303787.4

(51) Int. Cl.

| | | |
|---|---|---|
| A61K 9/14 | (2006.01) | |
| A61K 9/51 | (2006.01) | |
| C07K 14/47 | (2006.01) | |
| C07K 14/575 | (2006.01) | |
| A61K 38/17 | (2006.01) | |
| B82Y 5/00 | (2011.01) | |
| C07K 5/083 | (2006.01) | |
| A61K 38/00 | (2006.01) | |
| A61K 47/48 | (2006.01) | |
| A61K 38/22 | (2006.01) | |
| A61K 45/06 | (2006.01) | |

(52) U.S. Cl.
CPC ... *A61K 9/14* (2013.01); *A61K 9/51* (2013.01); *A61K 9/5123* (2013.01); *A61K 38/00* (2013.01); *A61K 38/1709* (2013.01); *A61K 38/22* (2013.01); *A61K 45/06* (2013.01); *A61K 47/48861* (2013.01); *A61K 47/48884* (2013.01); *B82Y 5/00* (2013.01); *C07K 5/0806* (2013.01); *C07K 14/47* (2013.01); *C07K 14/575* (2013.01)

(58) Field of Classification Search
USPC ................................. 506/1–43; 977/773–774
See application file for complete search history.

(56) References Cited

U.S. PATENT DOCUMENTS

| 2009/0011008 A1 | 1/2009 | Sung et al. | |
|---|---|---|---|
| 2011/0111002 A1* | 5/2011 | Pop ............................... | 424/422 |
| 2014/0220135 A1* | 8/2014 | Rademacher et al. ........ | 424/489 |
| 2014/0227186 A1* | 8/2014 | Rademacher et al. ......... | 424/9.2 |

FOREIGN PATENT DOCUMENTS

| WO | 02/32404 A2 | 4/2002 | |
|---|---|---|---|
| WO | 2004/108165 A2 | 12/2004 | |
| WO | 2005/091704 A2 | 10/2005 | |
| WO | 2005/116226 A2 | 12/2005 | |
| WO | 2006/037979 A2 | 4/2006 | |
| WO | 2007/015105 A2 | 2/2007 | |
| WO | 2007/122388 A2 | 11/2007 | |
| WO | 2011/154711 A1 | 12/2011 | |
| WO | WO 2011154711 A1 * | 12/2011 | .............. A61K 47/48 |

OTHER PUBLICATIONS

Park et al., Strategies for Oral Delivery of Macromolecule Drugs, Biotechnol. Bioprocesses Eng. 15:66-75 (2010).*
Ratner, et al., "Adjunctive Therapy with the Amylin Analogue Pramlintide Leads to a Combined Improvement in Glycemic and Weight Control in Insulin-Treated Subjects with Type 2 Diabetes," Diabetes Technol. Therapeutics 4:51-61 (2002).*
Huang, Shih-Hung et al., "Direct Binding and Characterization of Lipase onto Magnetic Nanoparticles", Biotechnol. Prog., 19: 1095-1100 (2003).
Vestal, Christy R. et al., "Effects of Surface Coordination Chemistry on the Magnetic Properties of MnFe2O4 Spinel Ferrite Nanoparticles", J. Am. Chem. Soc., 125: 9828-9833 (2003).
Neveu, S. et al., "Size-Selective Chemical Synthesis of Tartrate Stabilized Cobalt Ferrite Ionic Magnetic Fluid", J. Colloid and Interface Science, 255: 293-298 (2002).
Cao, YunWei Charles et al., "Nanoparticles with Raman Spectroscopic Fingerprints for DNA and RNA Detection", Science, 297: 1536-1540 (2002).
Guerreiro, Luiz Henrique et al., "Polymeric particles for the controlled release of human amylin", Colloids and Surfaces B: Biointerfaces, 94: 101-106 (2012).
Lund, Torben et al., "The influence of ligand organization on the rate of uptake of gold nanoparticles by colorectal cancer cells", Biomaterials, 32: 9776-9784 (2011).
International Search Report/Written Opinion, dated Apr. 24, 2014, issued in corresponding International Application No. PCT/GB2014/050344.

* cited by examiner

*Primary Examiner* — James H Alstrum Acevedo
*Assistant Examiner* — Thea D' Ambrosio
(74) *Attorney, Agent, or Firm* — Patrick J. Hagan; Dann, Dorfman, Herrell and Skillman, P.C.

(57) ABSTRACT

The present invention relates to amylin peptide-carrying nanoparticles, particularly for use in medicine, and includes methods for treatment of disorders, e.g., of blood glucose regulation. Nanoparticle composition comprise a nanoparticle comprising a core comprising a metal and/or a semiconductor; and a corona comprising a plurality of ligands covalently linked to the core, wherein said ligands comprise glutathione; and at least one amylin peptide that is non-covalently bound to the corona.

23 Claims, 4 Drawing Sheets

NANOPARTICLE PEPTIDE COMPOSITIONS

FIELD OF THE INVENTION

The present invention relates to peptide-carrying nanoparticles, particularly for use in medicine, and includes methods for treatment of disorders, e.g., of blood glucose regulation.

BACKGROUND TO THE INVENTION

The present invention is directed at compositions and products and methods of making and administering such compositions and products, including for the treatment of mammals and particularly humans.

Bioactive agents, such as peptides, frequently suffer from poor stability, particularly thermo-stability, which may limit the conditions to which the agents can be subjected during preparation, processing, storage and/or delivery. For example, amylin, GLP-1 and insulin find use in the control and treatment of, e.g., Type 1 & Type 2 diabetes mellitus. Medical preparations of peptides for human use are generally formulated with one or more preservatives and/or stabilisers. Moreover, limited gastrointestinal stability typically presents a barrier to effective oral administration of bioactive peptides.

WO 2011/154711 describes glyconanoparticles that have a gold core surrounded by a carbohydrate corona and which act as carriers for peptides such as insulin.

There remains an unmet need for further nanoparticle compositions capable of carrying and/or stabilising bioactive peptides, including amylin, and for methods of delivering such bioactive peptides to a subject.

The present invention addresses these and other needs.

BRIEF DESCRIPTION OF THE INVENTION

Broadly, the present invention relates to amylin peptide-carrying nanoparticle compositions. The present inventors have found that nanoparticles having a corona of glutathione ligands bind amylin peptide (in some cases with a binding capacity of around 50 amylin peptide molecules per nanoparticle). Nanoparticles as defined herein therefor provide a carrier for the formulation and delivery of amylin to subjects in need of amylin therapeutic treatment.

Accordingly, in a first aspect the present invention provides a nanoparticle composition comprising:
  (a) a nanoparticle comprising:
    (i) a core comprising a metal and/or a semiconductor;
    (ii) a corona comprising a plurality of ligands covalently linked to the core, wherein said ligands comprise glutathione; and
  (b) at least one amylin peptide that is non-covalently bound to the corona.

In accordance with any one of the aspects of the present invention, the amylin peptide may comprise a native amylin peptide, such as human amylin or rat amylin, or an amylin analogue. In some cases, the amylin peptide has at least 70%, 80%, 90%, 95% or 99% amino acid sequence with the full-length amino acid sequence set forth as SEQ ID NO: 2. In some cases, the amylin peptide comprises or consists of the full-length amino acid sequence KCNTATCATQRLANFLPHSSNNFGAILSSTN (SEQ ID NO: 2).

In some case, the amylin peptide has at least 70%, 80%, 90%, 95% or 99% amino acid sequence with the full-length amino acid sequence of human amylin set forth below as SEQ ID NO: 4. SEQ ID NO: 4 is the sequence of residues 34-70 of the complete 89 amino acid sequence of the human islet amyloid polypeptide set forth below as SEQ ID NO: 3 and disclosed under UniProt accession no. P10997, version 131, dated 3 Oct. 2012.

```
>sp|P10997|IAPP_HUMAN Islet amyloid polypeptide
OS = Homo sapiens GN = IAPP PE = 1 SV = 1
MGILKLQVFLIVLSVALNHLKATPIESHQVEKRKCNTATCATQRLANFLV
HSSNNFGAILSSTNVGSNTYGKRNAVEVLKREPLNYLPL.
(SEQ ID NO: 3 with SEQ ID NO: 4 shown underlined)

>sp|P10997|34-70
                                        (SEQ ID NO: 4)
KCNTATCATQRLANFLVHSSNNFGAILSSTNVGSNTY.
```

In certain cases in accordance with the present invention, the amylin peptide may be selected from the group consisting of:
  (i) a peptide comprising or consisting of an amino acid sequence having at least 70%, 80%, 90%, 95% or 99% amino acid sequence identity to the full-length sequence set forth in SEQ ID NO: 2 or 4;
  (ii) a peptide comprising or consisting of the full-length amino acid sequence set forth in SEQ ID NO: 2 or 4;
  (iii) a peptide comprising or consisting of a variant sequence of the full-length amino acid sequence set forth in SEQ ID NO: 2 or 4, wherein said variant differs by addition, deletion, substitution or modification of not more than 1, 2, 3, 4, 5, 6, 7, 8, 9 or not more than 10 amino acids from said full-length amino acid sequence set forth in SEQ ID NO: 2 or 4;
  (iv) a peptide comprising or consisting of a fragment of any one of (i)-(iii), said fragment having a sequence length of at least 15, 20, 25 or 30 amino acids.

Preferably, the amylin peptide exhibits biological activity of amylin. In particular, said amylin peptide of any one of (i)-(iv) may exhibit at least 50% of the activity of the amylin peptide of SEQ ID NO: 2 or at least 50% of the activity of the amylin peptide of SEQ ID NO: 4 in an in vitro or in vivo bioassay of amylin activity. In certain cases, the amylin activity may comprise reduction in post-prandial glucose excursion, inhibition of gastric secretion (e.g. secretion of one or more of gastric acid, pancreatic enzymes and bile ejection), inhibition of gastric emptying, and/or suppression of post-prandial glucagon secretion.

It has been found that the nanoparticles in accordance with the present invention may be provided with a variety of numbers of ligands forming the corona. For example, in some cases the corona comprises at least 5, 10, 20 or at least 50 ligands per core, e.g. between about 10 to about 1000 ligands per core. In particular, the nanoparticle compositions in accordance with any aspect of the present invention may comprise at least 5, 10, 20 or at least 50 glutathione ligands per core.

The number of amylin peptide molecules bound per core is not particularly limited. For certain applications, it may be desirable to employ as few as 1, 2, 3 or 4 amylin peptides per core, while in other cases the nanoparticle of the invention may comprise at least 5, 10, 20 or at least 50 or more amylin peptide molecules bound per core.

In some cases, in accordance with any one of the aspects of the present invention, the at least one amylin peptide may be bound to the corona of the nanoparticle in a reversible manner. In particular, the amylin peptide may be bound to the corona such that at least a fraction of the bound amylin peptide is released from the nanoparticle upon contacting the nanoparticle with a physiological solution.

In some cases, in accordance with any one of the aspects of the present invention, said ligands comprise glutathione alone or in conjunction with other species of ligand, e.g., combinations of glutathione and carbohydrate ligands (including glucose-containing ligands) are specifically contemplated herein.

In some cases, in accordance with any one of the aspects of the present invention, the nanoparticle comprises at least 10, at least 20, at least 30, at least 40 or at least 50 ligands which are (i) glutathione ligands; or (ii) both glutathione ligands and ligands other than glutathione, such as carbohydrate-containing ligands.

In some cases, in accordance with any one of the aspects of the present invention, the diameter of the core of the nanoparticle is in the range 1 nm to 5 nm.

In some cases, in accordance with any one of the aspects of the present invention, the diameter of the nanoparticle including its ligands is in the range 2 nm to 50 nm, optionally 3 nm to 30 nm, or 4 nm to 20 nm, or 5 nm to 15 nm.

In some cases, in accordance with any one of the aspects of the present invention, the core comprises a metal selected from the group consisting of: Au, Ag, Cu, Pt, Pd, Fe, Co, Gd and Zn, or any combination thereof.

In some cases, in accordance with any one of the aspects of the present invention, the core is magnetic.

In some cases, in accordance with any one of the aspects of the present invention, the core comprises a semiconductor. The semiconductor may comprise metal atoms, such as cadmium. Alternatively or additionally, the semiconductor may comprise non-metal atoms. Organic semiconductors are specifically contemplated herein. Preferred semiconductors, in accordance with the present invention, may be selected from the group consisting of: cadmium selenide, cadmium sulphide, cadmium tellurium and zinc sulphide.

In some cases, in accordance with any one of the aspects of the present invention, the core is capable of acting as a quantum dot.

Preferably, the composition in accordance with the first aspect of the invention comprises a plurality, e.g., 100, 1000, 100000, or more, of said nanoparticles, wherein at least 10%, 20%, 30%, 40%, 50%, 60%, 70%, 80%, 90% or 95% of the nanoparticles in said composition have at least one amylin peptide bound.

In some cases, in accordance with any one of the aspects of the present invention, the nanoparticle composition comprises a carrier, such as solution, a polymer, a powder, or a cream, in which the nanoparticles and bound amylin peptides are suspended. The composition may be in an associated form, a suspension or contained together in a single package, container or carrier. In certain cases, the composition may take the form of one or more doses (e.g. a defined quantity of amylin peptide or amylin peptide activity units), such as in the form of a therapeutic dose or defined number of doses.

In some cases, in accordance with any one of the aspects of the present invention, the nanoparticle composition further comprises at least one permeation enhancer that is non-covalently or covalently bound to said core and/or or said corona. As described in co-pending GB patent application No. 1301991.4, filed 5 Feb. 2013, the entire contents of which are expressly incorporated herein by reference for all purposes, and co-pending international application, PCT/GB2014/050301, filed 4 Feb. 2014, the entire contents of which are expressly incorporated herein by reference for all purposes, certain permeation enhancers may be advantageously bound to the nanoparticle without displacing any significant active peptide, such as the amylin peptide as defined herein. In certain cases, said permeation enhancer is selected from an alkyl-D-maltoside (e.g. tetradecyl-D-maltoside, dodecyl-β-D-maltoside, hexyl-β-D-maltoside, octyl-β-D-maltoside, nonyl-β-D-maltoside, decyl-β-D-maltoside, undecyl-β-D-maltoside, tridecyl-β-D-maltoside, or hexadecyl-β-D-maltoside) and lysalbinic acid. In certain cases, said permeation enhancer, e.g. tetradecyl-D-maltoside, dodecyl-β-D-maltoside and/or lysalbinic acid is non-covalently bound to said corona.

In a second aspect, the present invention provides a nanoparticle composition as defined in accordance with the first aspect, for use in medicine.

In a third aspect, the present invention provides a nanoparticle composition as defined in accordance with the first aspect, for use in a method of treatment of a disorder of glucose regulation in a mammalian subject.

In a fourth aspect, the present invention provides use of a nanoparticle composition as defined in accordance with the first aspect in the preparation of a medicament for treatment of a disorder of glucose regulation in a mammalian subject.

In a fifth aspect, the present invention provides a method of treatment of a disorder of glucose regulation in a mammalian subject, the method comprising administering a therapeutically effective amount of a nanoparticle composition as defined in accordance with the first aspect to the subject in need of said treatment.

In a sixth aspect, the present invention provides a method of lowering a blood glucose level in a mammalian subject, the method comprising administering an effective amount of a nanoparticle composition as defined in accordance with the first aspect to the subject.

In accordance with any one of the second to sixth aspects of the invention, the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human.

In accordance with any one of the second to sixth aspects of the invention, the subject may have a disorder that results in improper control of blood glucose levels. In particular, specifically contemplated herein is a subjects having diabetes mellitus (Type 1, Type 2, gestational, or prediabetes). The subject may or may not have previously been diagnosed with diabetes mellitus. For example, the subject may have been identified as being at risk of developing diabetes mellitus. The subject may, in some cases, be following a course of treatment for diabetes mellitus. In particular, the subject may be taking, or have been advised to take, insulin.

In accordance with any one of the second to sixth aspects of the invention, the nanoparticle composition may be administered or for administration with (i.e. simultaneously, separately or sequentially) one or more therapeutic agents for the control of blood glucose. In particular, the nanoparticle composition may be administered or for administration with one or more therapeutic agents selected from the group consisting of: insulin or analogue thereof, GLP-1 or analogue thereof, gastric inhibitory peptide (GIP) or analogue thereof, Dipeptidyl peptidase-4 (DPP-4) inhibitor, sulfonylurea, metformin, alpha-glucosidase inhibitor, and thiazolidinediones. Combination therapy has considerable potential to enhance the therapeutic effect of the nanoparticle compositions of the present invention. Specific combinations contemplated herein include: (i) insulin or analogue thereof together with the nanoparticle compositions of the present invention; (ii) GLP-1 or analogue thereof together with the nanoparticle compositions of the present invention; (iii) insulin-carrying nanoparticles as disclosed in WO 2011/154711 together with the nanoparticle compositions of the present invention, (iv)

GLP-1-carrying nanoparticles as disclosed in WO 2011/154711 together with the nanoparticle compositions of the present invention; and (v) insulin and GLP-1-carrying nanoparticles as disclosed in WO 2011/154711 (see, e.g., claim 48 thereof) together with the nanoparticle compositions of the present invention.

In accordance with any one of the second to sixth aspects of the invention, the nanoparticle composition may be administered or for administration by any suitable route. In particular cases, the nanoparticle composition may be administered or for administration via a route selected from the group consisting of: intravenous (i.v.), intramuscular (i.m.), intradermal (i.d.), intraperitoneal or subcutaneous (s.c.) injection or infusion; buccal; sublabial; sublingual; by inhalation; via one or more mucosal membranes; urogenital; rectal; and dermal.

In a seventh aspect, the present invention provides an article of manufacture comprising:
  a nanoparticle composition as defined in accordance with the first aspect of the invention;
  a container for housing the nanoparticle composition; and
  an insert and/or label. Preferably, the insert and/or label provide instructions, dosage and/or administration information relating to the use of the nanoparticle composition in a method of treatment of a disorder of glucose regulation. In particular, the disorder may be diabetes mellitus type I or type II or gestational diabetes.

In an eighth aspect, the present invention provides a process for producing a nanoparticle composition as defined in accordance with the first aspect of the invention, the process comprising:
  providing a nanoparticle comprising a core comprising a metal and/or a semiconductor and a corona comprising a plurality of ligands covalently linked to the core, wherein said ligands comprise glutathione; and
  contacting the nanoparticle with at least one amylin peptide under conditions which allow the at least one amylin peptide to bind to the corona of the nanoparticle.

In some cases, in accordance with this aspect of the present invention, the process comprises an earlier step of producing the nanoparticle, said earlier step comprising: combining a solution comprising glutathione with a solution comprising a core-forming material (e.g. gold III chloride) and with a reducing agent (e.g. sodium borohydride), thereby causing the nanoparticle to self-assemble.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
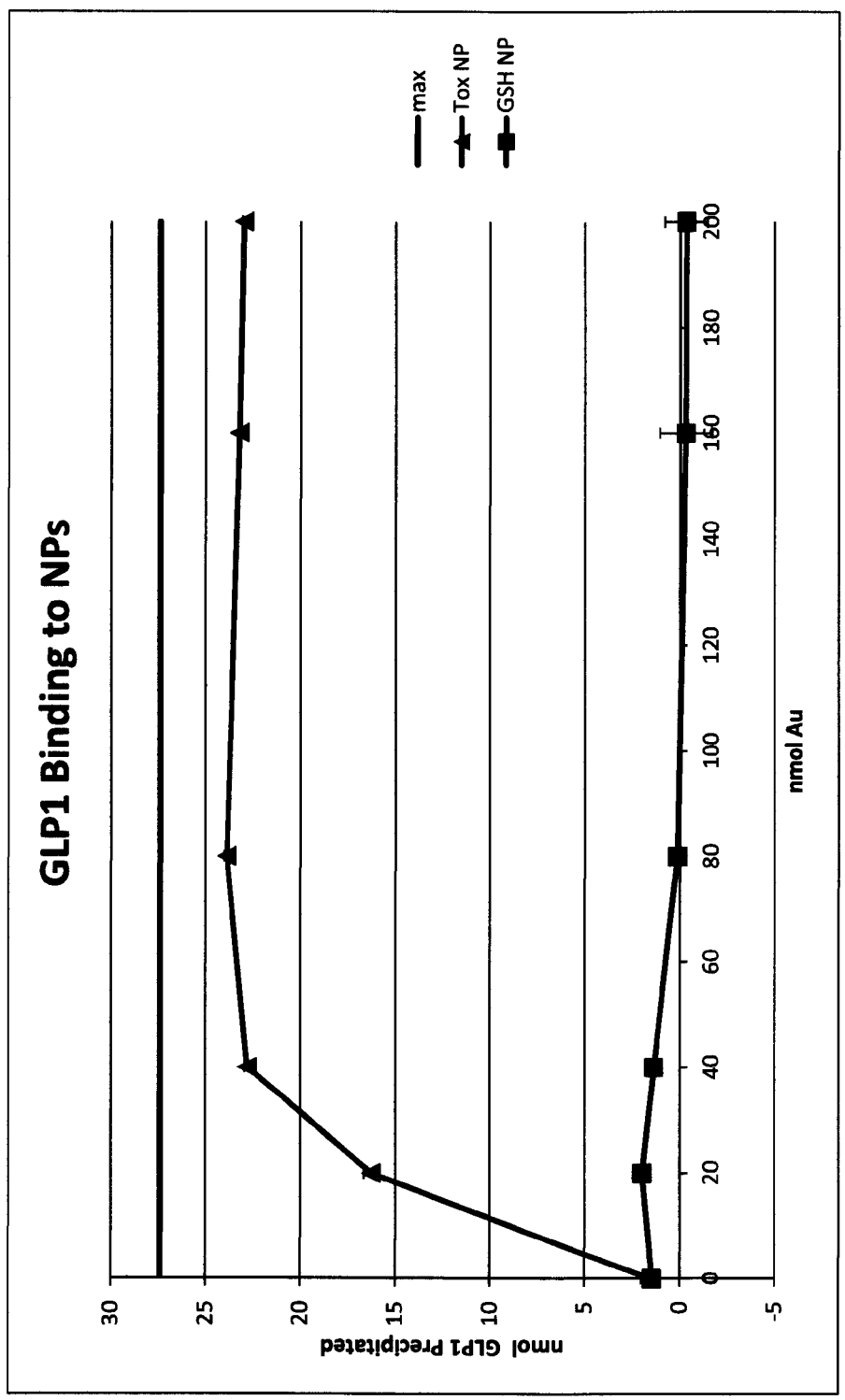
FIG. 1 shows the binding of the Val(8)GLP-1 peptide to nanoparticles having a corona of alpha-galactose ligands and aminolinker ligands ("Tox NP"—triangles) and to nanoparticles having a corona of glutathione ligands ("GSH NP"—squares). The GLP-1 peptide exhibits greater binding to the Tox NPs in comparison with the GSH NPs.

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in EP2305310 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which generally include at least one carbohydrate moiety, one surfactant moiety and/or one glutathione moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the semiconductor or metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 20 nm, more preferably between 3 and 10 nm and most preferably between 4 and 5 nm. The mean diameter can be measured using techniques well known in the art such as transmission electron microscopy.

The core material can be a metal or semiconductor (said semiconductor optionally comprising metal atoms or being an organic semiconductor) and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor compounds can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and about 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{58}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

Amylin Peptide

In certain cases in accordance with the present invention, the "amylin peptide" may be selected from the group consisting of:
 (i) a peptide comprising or consisting of an amino acid sequence having at least 70%, 80%, 90%, 95% or 99% amino acid sequence identity to the full-length sequence set forth in SEQ ID NO: 2 or 4;
 (ii) a peptide comprising or consisting of the full-length amino acid sequence set forth in SEQ ID NO: 2 or 4;

(iii) a peptide comprising or consisting of a variant sequence of the full-length amino acid sequence set forth in SEQ ID NO: 2 or 4, wherein said variant differs by addition, deletion, substitution or modification of not more than 1, 2, 3, 4, 5, 6, 7, 8, 9 or not more than 10 amino acids from said full-length amino acid sequence set forth in SEQ ID NO: 2 or 4;

(iv) a peptide comprising or consisting of a fragment of any one of (i)-(iii), said fragment having a sequence length of at least 15, 20, 25 or 30 amino acids.

Preferably, said amylin peptide of any one of (i)-(iv) exhibits biological activity of amylin. In particular, said amylin peptide of any one of (i)-(iv) may exhibit at least 50% of the activity of the amylin peptide of SEQ ID NO: 2 or at least 50% of the activity of the amylin peptide of SEQ ID NO: 4 in an in vitro or in vivo bioassay of amylin activity. In certain cases, the amylin activity may comprise reduction in post-prandial glucose excursion, inhibition of gastric secretion (e.g. secretion of one or more of gastric acid, pancreatic enzymes and bile ejection), inhibition of gastric emptying, and/or suppression of post-prandial glucagon secretion.

The amylin peptide is bound to the corona of the nanoparticle. Without wishing to be bound by any theory, it is presently believed that the amylin peptide may participate in one or more reversible binding interactions with one or more ligands that provide the corona of the nanoparticle. In particular, a portion of the sequence of amino acids may participate in hydrogen bonding, Van der Waals forces and/or electrostatic interactions with one or more ligands (e.g. interacting with one or more glutathione ligands). The peptide binding may involve adsorption, absorption or other direct or indirect interaction with one or more ligands of the nanoparticle.

As described herein with reference to certain embodiments of the present invention, the amylin peptide may be bound such that at least a fraction or portion of the bound amylin peptide is released from the nanoparticle upon contacting the nanoparticle with a physiological solution. As described herein the amylin peptide may be bound to the nanoparticle in a manner such that the amylin peptide is stabilised (e.g. thermostabilised) while bound, but is releasable and available in a form that is biologically active (for example, releasable such that the amylin peptide is detectable by ELISA and/or capable of exerting at least one biological action in an in vitro or in vivo assay system that is characteristic of the free amylin peptide). In particular, the amylin peptide may be bound to the nanoparticle such that a suspension of the amylin-bound nanoparticles gives a positive result in an ELISA for, e.g., (human) amylin and/or exerts an effect on post-prandial glucose excursion in a mammalian subject.

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, or ballistically using a delivery gun to accelerate their transdermal passage through the outer layer of the epidermis. The nanoparticles may also be delivered in aerosols. This is made possible by the small size of the nanoparticles.

The nanoparticles of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. intravenously, orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

The following is presented by way of example and is not to be construed as a limitation to the scope of the claims.

EXAMPLES

Example 1

Synthesis of Nanoparticles

Gold nanoparticles having a corona of carbohydrate ligands or glutathione ligands were synthesised essentially as described previously (WO 2011/154711; and Lund et al., 2011, Biomaterials Vol. 32 pp. 9776-9784, the entire contents of which are expressly incorporated herein by reference).

AL/α-Gal NPs (Tox Batch)

Preparation of 2-thio-ethyl-α-D-galactoside (α-galactose C2SH)

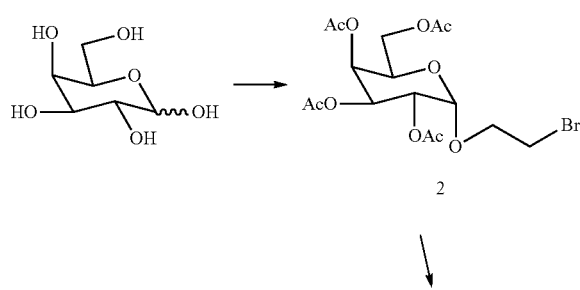

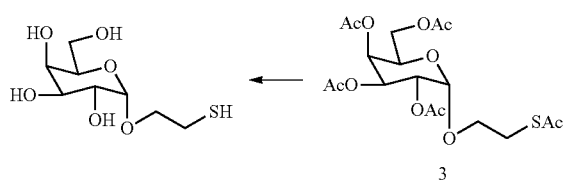

To a suspension of galactose (3 g, 16.65 mmol) in 2-bromoethanol (30 ml), acid resin Amberlite 120-His added to reach pH 2. The reaction is stirred for 16 hours at 50-60° C. The reaction mixture is filtered and washed with MeOH. Triethylamine is added to reach pH 8. The crude of the reaction is concentrated and co evaporated 3 times with toluene. The reaction mixture is dissolved pyridine (75 mL) and Ac2O (35 mL) and a catalytic amount of DMAP are added at 0° C. and stirred for 3 h at rt. The mixture is diluted with AcOEt and washed with 1. H$_2$O; 2. HCl (10%) 3. NaHCO$_3$ dis 4. H$_2$O. The organic layer is collected and dried over anhydrous Na$_2$SO$_4$. TLC (Hexane:AcOEt 3:1, 2 elutions) shows a major product (desired) and a lower Rf minority. The product is purified by flash chromatography using the mixture hexane:ethyl acetate 6:1 as eluyent and the 2-bromoethyl-alpha-galactoside (2) is obtained.

The product of the previous reaction, 2 is dissolved in 27 ml of 2-butanone. To this solution, a catalytic amount of tetrabutylammonium iodide and 4 equivalents of potassium thioacetate are added. The resulting suspension is stirred for 2 hours at room temperature. Throughout this period the reaction is tested by TLC (hexane-AcOEt 2:1, 2 elutions) for the disappearance of the starting material. The mixture is diluted with 20 ml of AcOEt and washed with a saturated NaCl solution. The organic phase is dried, filtered and evaporated under vacuum. The product is purified in hexane/AcOEt 2:1→1:1 to obtain the acetylthio-alpha-galactoside 3.

The new product of the reaction, 3 is dissolved in a mixture dichloromethane-methanol 2:1. To this mixture a solution of 1N sodium methoxide (1 equivalent) is added and stirred for 1 hour at room temperature. Amberlite IR-120H resin is added to achieve pH 5-6. The resulting mixture is then filtered and concentrated to dryness to obtain the final product (α-galactose C2SH).

Preparation of Amino-Thiol Linker.

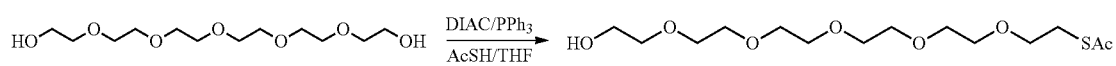

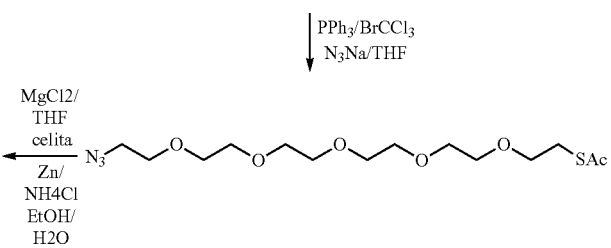

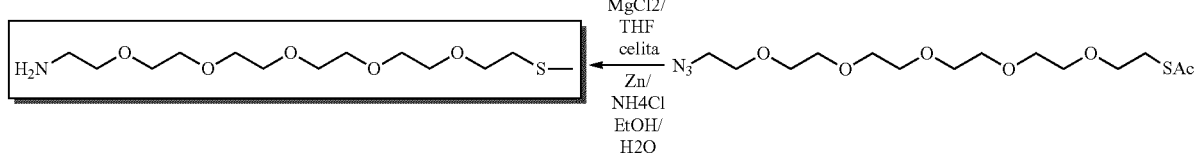

To a solution of PPh$_3$ (3 g, 11.4 mmol) in 20 ml dry THF, DIAC (2.3 g, 11.4 mmol) is added. The mixture is allowed to stir at 0° C. 15 min until the appearance of a white product. To this mixture a solution of hexaethyleneglycol (1.45 mL, 5.7 mmol) and HSAc (610 μl, 8.55 mmol) in dry THF (20 mL) is added dropwise (addition funnel). After 15 min the products begin to appear on TLC at Rf 0.2. The solution is concentrated in an evaporator. The crude of the reaction is dissolved in 50 ml of dichloromethane and washed with a solution of K$_2$CO$_3$ 10%. The organic phase is dried over anhydrous Na$_2$SO$_4$, filtered and concentrated under vacuum. Flash chromatography of the crude using AcOEt:Hexane 1:1, AcOEt and finally DCM:MeOH 4:1 as eluyent gave the acetyl-thio-hexaethyleneglycol derivative.

The reaction product is dissolved in 5 ml of DMF and PPh$_3$ (2.25 g, 8.55 mmol), NaN$_3$ (0.741 g, 11.4 mmol) and BrCl$_3$C (0.845 ml, 8.55 mmol) are added and the solution subsequently stirred for 40 min at room temperature. The resulting product has a higher Rf than the starting product when performing TLC (DCM:MeOH 25:1). The reaction mixture is diluted with 100 ml of diethylether and washed three times with H$_2$O. The organic phase is dried over anhydrous Na$_2$SO$_4$, filtered and evaporated under vacuum. The product is purified by flash chromatography using the mixture of eluyents DMC/MeOH 200:1 and DCM/MeOH 40:1 to obtain the azido-acetylthio-hexaethyleneglycol derivative.

To remove the triphenyl phosphine oxide, the reaction product is dissolved in 10 ml of THF and 0.5 g of MgCl$_2$ is added to this solution. The reaction is stirred for 2 h at 80° C. until a white precipitate appears and then is filtered through celite. The product is dissolved in a mixture of ethanol:H$_2$O 3:1 and added Zn dust (0.45 g, 6.84 mmol) and NH$_4$Cl (0.6 g, 11.4 mmol). The reaction was stirred at reflux for 1 h until the presence of starting material is no longer detectable by TLC (DCM/MeOH 25:1). The reaction is filtered through celite and the solvent is evaporated. The crude de reaction is diluted with AcOEt and extract with 5 ml H$_2$O. The aqueous phase is evaporated to dryness to obtain the amino-thiol-hexaethylenglycol product.

Alpha-galactose C2 derivative 3 and hexaethyleneglycol amine linker 6 were taken from Midatech Biogune stock. N-(3-Dimethylaminopropyl)-N'-ethylcarbodiimide hydrochloride (EDC.HCl), HAuCl$_4$, NaBH$_4$ were purchased from Sigma-Aldrich Chemical Company. Imidazole-4-acetic acid monohydrochloride was purchased from Alfa Aesar. Company High quality MeOH and Nanopure water (18.1 nΩ) were used for all experiments and solutions.

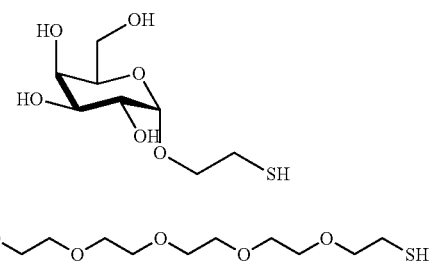

α-GalC2 (alpha)

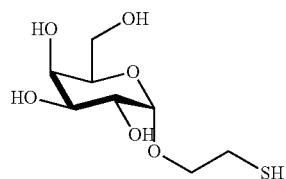

2'-thioethyl-α-D-galactopyranoside (alpha)
EG6NH2

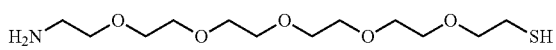

1-amino-17-mercapto-3,6,9,12,15,-pentaoxa-heptadecanol or 1-amino-6-mercapto-hexaethylenglycol (vulgar name)

Preparation of AL/α-Gal NPs (Tox batch): To a mix of amine-mercapto hexaethylenglycol linker 6 and alpha-galactose ligand 3 in a ratio 1:1 (0.58 mmol, 3 eq.) in MeOH (49 mL) was added an aqueous solution of gold salt (7.86 mL, 0.19 mmol, 0.025M). The reaction was stirred for 30 seconds and then, an aqueous solution of NaBH$_4$ (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

GSH NPs

Oxidized ligand, glutathione (Fluka 49741) was dissolved in 9:1 methanol:water and gold III chloride (Sigma-Aldrich, Poole, UK) added. The organic ligand was used at a fourfold molar excess relative to the gold. The solution was then mixed for 5 min gently on a flat-bed shaker. The nanoparticles were produced by reduction following the rapid addition of a 20 fold molar excess relative to the gold, of freshly made 1 M sodium borohydride (Sigma-Aldrich, Poole, UK) under vigorous vortexing. The samples were vortexed for a total of 30 s followed by a further 1 h gentle mixing on the flat bed shaker. As the nanoparticles are not soluble in methanol/water solvent, initial purification was by bench centrifugation, supernatant removal and dispersion of the nanoparticle pellet in water. Further purification was achieved by 4 water washes in 10 kDa vivaspin centrifugation devices (GE Healthcare). The gold concentration of all nanoparticle preparations was determined by a simple colorimetric assay. Briefly 10 µl of nanoparticle sample or 12 mg/ml gold standard (Fluka (Sigma-Aldrich, Poole, UK)) and blanks were digested with 30 µl of 50:50 water:aqua regia in an ELISA plate for 1 min, this was followed by addition of 150 µl of 2 M NaBr, the 405 nm absorbance was then measured immediately, the assay having excellent linearity over the 0-10 µg range.

Example 2

Peptide Binding to Nanoparticles

The present inventors have investigated the ability of the following two peptides to nanoparticles as described herein:
1. a long-lasting GLP-1 analogue Val(8)GLP-1: HVEGTFTSDVSSYLEGQAAKEFIAWLVKGR (SEQ ID NO: 1); and
2. an Amylin analogue V17 to P17: KCNTATCATQRLANFLPHSSNNFGAILSSTN (SEQ ID NO: 2).

Figure 2:
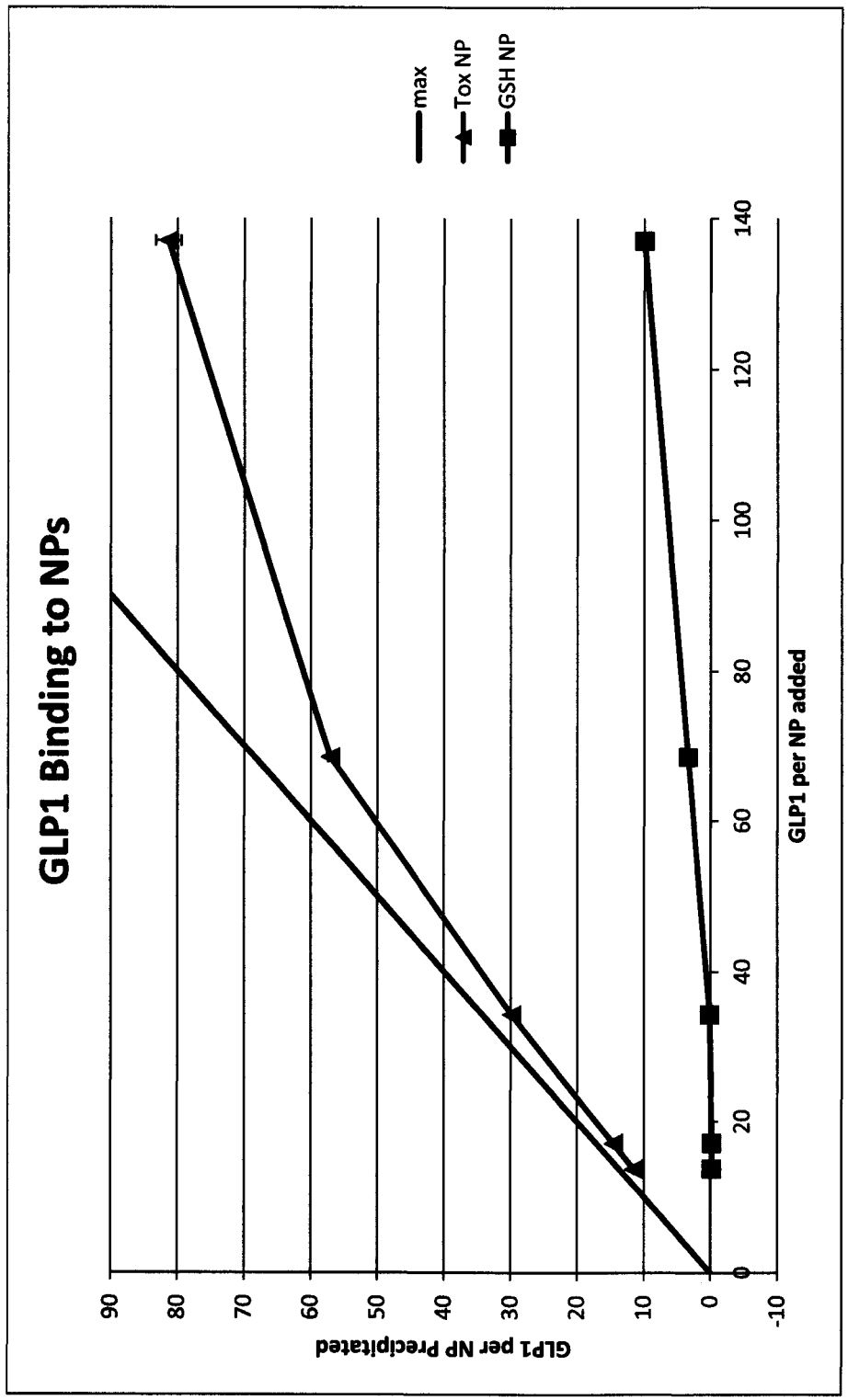
FIG. 2 shows the binding capacity (molecules of peptide per nanoparticle core) of the Val(8)GLP-1 peptide to nanoparticles having a corona of alpha-galactose ligands and aminolinker ligands ("Tox NP"—triangles) and to nanoparticles having a corona of glutathione ligands ("GSH NP"—squares). The GLP-1 peptide exhibits greater binding capacity (approximately 80 per NP) to the Tox NPs in comparison with the GSH NPs (approximately 10 per NP).

Following the procedure for insulin binding (see Example 3 of WO 2011/154711, the contents of which are expressly incorporated herein by reference), GLP-1 was successfully bound to AL/αGal NPs (see FIGS. 1 and 2). The only precautionary change to the methodology was to dissolve GLP-1 in the 20 mM pH 8.0 Tris/HCl buffer directly instead of in HCl initially to avoid potential damage to the peptide.

Probably due in part to the lower molecular weight of Val(8)GLP-1 (3384 g/mol) in comparison to insulin, Val(8) GLP-1 appears to bind with greater capacity to the AL/αGal NPs. Binding capacity >80 Val(8)GLP-1 per nanoparticle (see FIG. 2).

Figure 3:
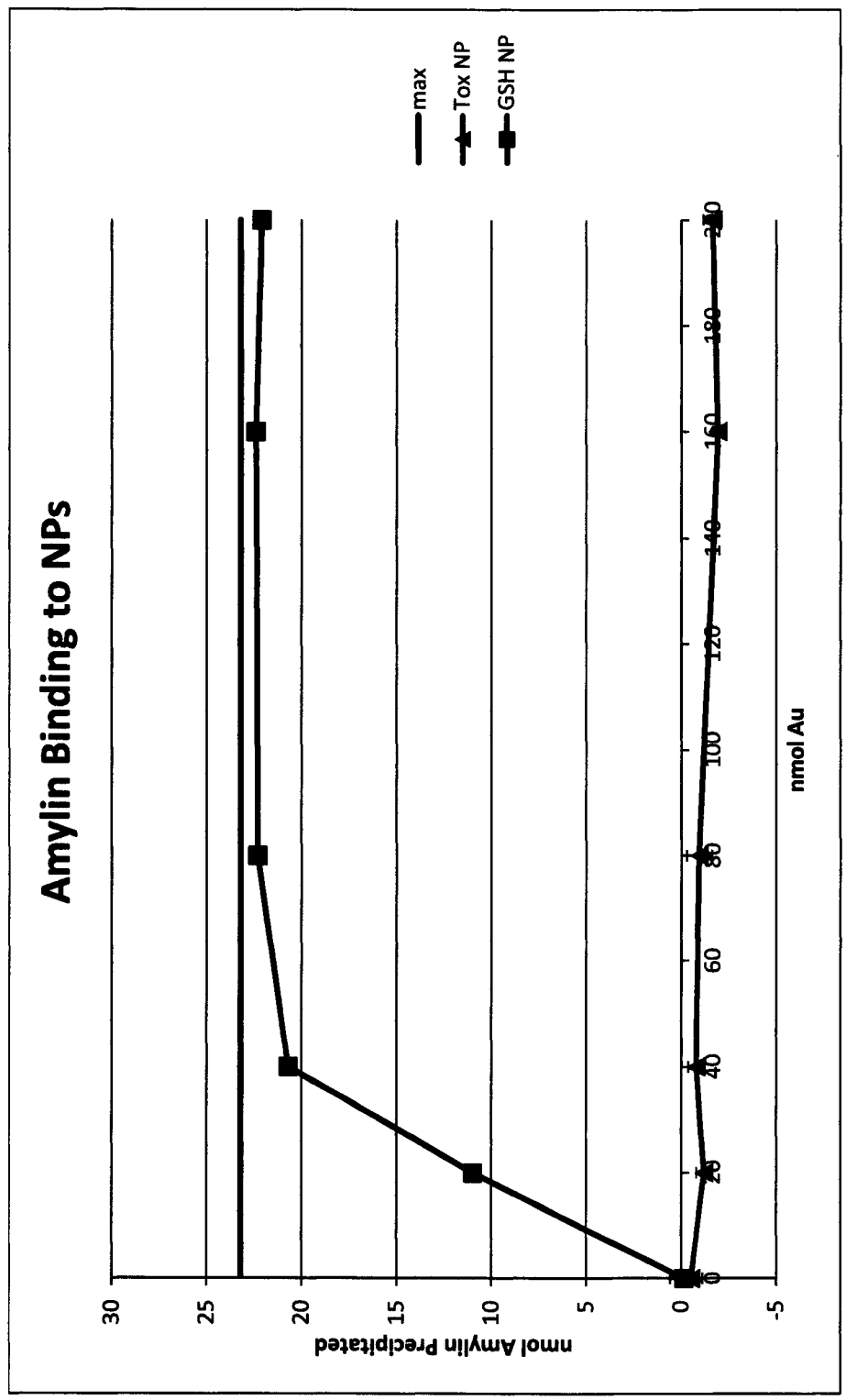
FIG. 3 shows the binding of the amylin peptide to nanoparticles having a corona of alpha-galactose ligands and aminolinker ligands ("Tox NP"—triangles) and to nanoparticles having a corona of glutathione ligands ("GSH NP"—squares). The amylin peptide exhibits greater binding to the GSH NPs in comparison with the Tox NPs.
Figure 4:
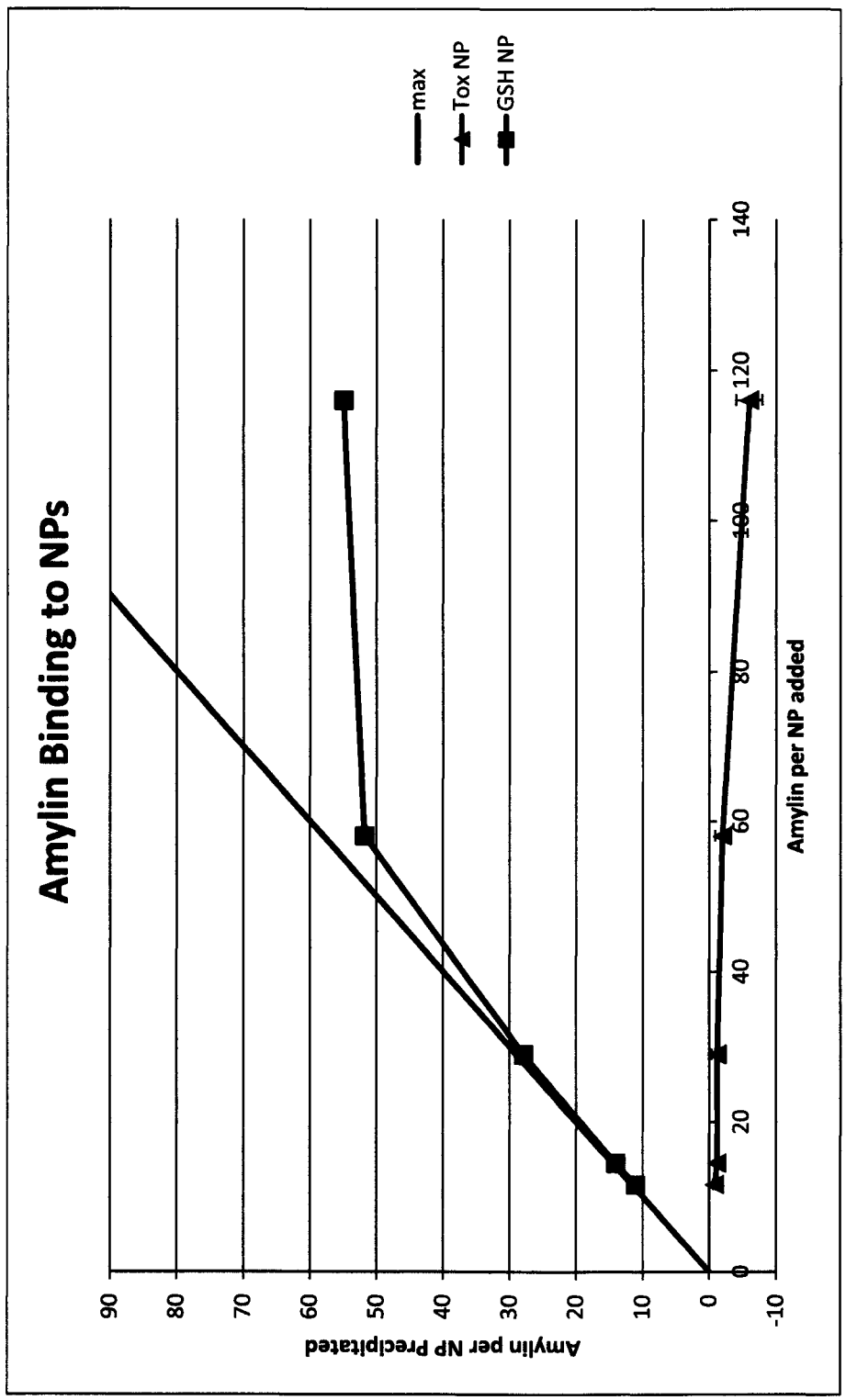
FIG. 4 shows the binding capacity (molecules of peptide per nanoparticle core) of the amylin peptide to nanoparticles having a corona of alpha-galactose ligands and aminolinker ligands ("Tox NP"—triangles) and to nanoparticles having a corona of glutathione ligands ("GSH NP"—squares). The amylin peptide exhibits greater binding capacity (approximately 50-55 per NP) to the GSH NPs in comparison with the Tox NPs (essentially zero binding).

Following the standard procedure for insulin binding (see Example 3 of WO 2011/154711, the contents of which are expressly incorporated herein by reference), Amylin was successfully bound to GSH NPs (see FIGS. 3 and 4). As before, Amylin was also dissolved in the Tris/HCl buffer directly.

The AL/αGal NPs (Tox batch) show little or no capacity to bind amylin (see FIGS. 3 and 4). Without wishing to be bound by any particular theory, the present inventors believe that the lack of bind of amylin to the AL/αGal NPs may be due to lack of electrostatic attraction.

GSH NPs appear to achieve a binding capacity of >50 amylin peptides per nanoparticle (see FIG. 4). This is relatively high when compared to insulin binding results, but as with Val(8)GLP-1 this is thought to be due, at least in part, to the somewhat lower molecular weight (3904 g/mol) of amylin vs. insulin.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

---

The invention claimed is:

1. A nanoparticle composition comprising:
   (a) a nanoparticle comprising:
      (i) a core comprising a metal and/or a semiconductor;
      (ii) a corona comprising a plurality of ligands covalently linked to the core,
   wherein said ligands comprise glutathione; and
   (b) at least one amylin peptide that is non-covalently bound to the corona, wherein said amylin peptide has an amino acid sequence that is at least 95% identical to the full-length sequence set forth in SEQ ID NO: 2 or 4.

2. The nanoparticle composition according to claim 1, wherein the amino acid sequence of said amylin peptide consists of the amino acid sequence set forth in SEQ ID NO: 2 or 4.

3. The nanoparticle composition according to claim 1, wherein the corona comprises at least 5, 10, 20 or 50 ligands per core.

4. The nanoparticle composition according to claim 1, wherein the corona comprises at least 5, 10, 20 or 50 glutathione ligands per core.

5. The nanoparticle composition according to claim 1, wherein the number of amylin peptides bound to the nanoparticle comprises: 1, 2, 3, 4, 5, 10, 20, or at least 50 per core.

6. The nanoparticle composition according to claim 1, wherein the at least one amylin peptide is bound to the corona of the nanoparticle in a reversible manner.

7. The nanoparticle composition according to claim 1, wherein the amylin peptide is bound to the corona such that at least a fraction of the bound amylin peptide is released from the nanoparticle upon contacting the nanoparticle composition with a physiological solution.

8. The nanoparticle composition according to claim 1, wherein said ligands comprise glutathione alone or in conjunction with other species of ligand.

9. The nanoparticle composition according to claim 8, wherein said ligands comprise combinations of glutathione and carbohydrate ligands.

10. A pharmaceutical composition comprising a plurality of nanoparticles and at least one pharmaceutically acceptable excipient, carrier, buffer, stabilizer, isotonicizing agent, preservative or anti-oxidant, wherein at least 10%, 20%, 30%, 40%, 50%, 60%, 70%, 80%, 90% or 95% of the nanoparticles in said composition are the nanoparticles of claim 1 having at least one of said amylin peptides bound.

11. The pharmaceutical composition according to claim 10, wherein the composition is in an associated form, a suspension or contained in a single package or container.

12. The pharmaceutical composition according to claim 10, wherein the composition is in the form of one or more doses of a defined (i) quantity of said amylin peptide, or (ii) a level of said amylin peptide activity units.

13. The pharmaceutical composition according to claim 10, wherein the composition further comprises at least one permeation enhancer that is non-covalently or covalently bound to said core and/or said corona.

14. The pharmaceutical composition according to claim 13, wherein said permeation enhancer is selected from the group consisting of: an alkyl-D-maltoside, tetradecyl-D-maltoside, dodecyl-β-D-maltoside, hexyl-β-D-maltoside, octyl-β-D-maltoside, nonyl-β-D-maltoside, decyl-β-D-maltoside, undecyl-β-D-maltoside, tridecyl-β-D-maltoside, hexadecyl-β-D-maltoside and lysalbinic acid.

15. The pharmaceutical composition according to claim 14, wherein said permeation enhancer is non-covalently bound to said corona.

16. A method of treatment of a disorder of glucose regulation in a mammalian subject, the method comprising administering a therapeutically effective amount of the nanoparticle composition of claim 1 to the subject in need of said treatment.

17. A method of lowering a blood glucose level in a mammalian subject, the method comprising administering an effective amount of the nanoparticle composition of claim 1 to the subject in need thereof.

18. The method of claim 17, wherein said blood glucose level is basal, fasting or post-prandial.

19. The method of claim 16, wherein the subject has type 1 diabetes mellitus, type 2 diabetes mellitus, gestational diabetes or prediabetes.

20. The method of claim 16, wherein the nanoparticle composition is administered simultaneously, separately or sequentially with one or more therapeutic agents for the control of blood glucose selected from the group consisting of: insulin or analogue thereof, GLP-1 or analogue thereof, gastric inhibitory peptide (GIP) or analogue thereof, Dipeptidyl peptidase-4 (DPP-4) inhibitor, sulfonylurea, metformin, alpha-glucosidase inhibitor, and thiazolidinediones.

21. The method of claim 16, wherein the nanoparticle composition is administered via a route selected from the group consisting of: intravenous (i.v.), intramuscular (i.m.), intradermal (i.d.), intraperitoneal infection, subcutaneous (s.c.) injection, infusion; buccal; sublabial; sublingual; by inhalation; via one or more mucosal membranes; urogenital; rectal; and dermal.

22. An article of manufacture comprising:
   the nanoparticle composition of claim 1;
   a container for housing the nanoparticle composition; and
   an insert and/or label.

23. A process for producing the nanoparticle composition of claim 1, the process comprising:
Providing a nanoparticle comprising a core comprising a metal and/or a semiconductor and a corona comprising a plurality of ligands covalently linked to the core, wherein said ligands comprise glutathione; and
contacting the nanoparticle with at least one amylin peptide under conditions which allow the at least one amylin peptide to non-covalently bind to the corona of the nanoparticle, wherein said amylin peptide has an amino acid sequence that is at least 95% identical to the full-length sequence set forth in SEQ ID NO: 2 or 4.

* * * * *

SEQUENCE LISTING

```
<160> NUMBER OF SEQ ID NOS: 4

<210> SEQ ID NO 1
<211> LENGTH: 30
<212> TYPE: PRT
<213> ORGANISM: Artificial sequence
<220> FEATURE:
<223> OTHER INFORMATION: Synthetic sequence: GLP-1 analogue Val (8) GLP-
      1

<400> SEQUENCE: 1

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Artificial sequence
<220> FEATURE:
<223> OTHER INFORMATION: Synthetic sequence: Amylin analogue V17 to P17

<400> SEQUENCE: 2

Lys Cys Asn Thr Ala Thr Cys Ala Thr Gln Arg Leu Ala Asn Phe Leu
1               5                   10                  15

Pro His Ser Ser Asn Asn Phe Gly Ala Ile Leu Ser Ser Thr Asn
            20                  25                  30

<210> SEQ ID NO 3
<211> LENGTH: 89
<212> TYPE: PRT
<213> ORGANISM: Homo sapiens

<400> SEQUENCE: 3

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85
```

```
-continued

<210> SEQ ID NO 4
<211> LENGTH: 37
<212> TYPE: PRT
<213> ORGANISM: Homo sapiens

<400> SEQUENCE: 4

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
            35
```